United States Patent [19]

Hagemeyer et al.

[11] Patent Number: 5,780,700
[45] Date of Patent: Jul. 14, 1998

[54] CATALYTIC OXIDATIVE DEHYDROGENATION OF ALKYLAROMATICS AND PARAFFINS

[75] Inventors: Alfred Hagemeyer; Thomas Lautensack; Otto Watzenberger, all of Ludwigshafen; Axel Deimling, Neustadt, all of Germany

[73] Assignee: BASF Aktiengesellschaft, Ludwigshafen, Germany

[21] Appl. No.: 527,683

[22] Filed: Sep. 13, 1995

[51] Int. Cl.$^6$ ..................................................... C07C 5/09
[52] U.S. Cl. ............................................................ 585/617
[58] Field of Search ................................................ 585/617

[56] References Cited

U.S. PATENT DOCUMENTS

| | | | |
|---|---|---|---|
| 3,118,007 | 1/1964 | Kronig et al. | 585/617 |
| 3,440,299 | 4/1969 | Woskow et al. | 260/680 |
| 4,396,537 | 8/1983 | Eastman | 252/437 |

FOREIGN PATENT DOCUMENTS

| | | |
|---|---|---|
| 397637 | 11/1990 | European Pat. Off. |
| 403462 | 12/1990 | European Pat. Off. |
| 482276 | 4/1992 | European Pat. Off. |

*Primary Examiner*—C. Warren Ivy
*Assistant Examiner*—Lyman H. Smith
*Attorney, Agent, or Firm*—Keil & Weinkauf

[57] ABSTRACT

A process for the preparation of olefinically unsaturated compounds by catalytic oxidation, ie oxidative dehydrogenation by transferring oxygen from a previously oxidized oxygen carrier acting as catalyst, in the absence of molecular oxygen, the catalyst being regenerated after exhaustion, wherein, during the operating phase of the catalyst (oxidation/dehydration partial step), the residence time, space velocity and/or temperature of the reactants in the reactor is/are adjusted, ie, controlled, continuously or in discrete steps, in a manner appropiate to the momentary state of activity of the redox catalyst by adjusting—continuously or stepwise—the residence time of the reactants in the freshly regenerated catalyst (ie at the commencement of the reaction) to a shorter time, and/or the temperature to a lower value, than the corresponding parameter(s) in the partially reduced catalyst.

11 Claims, No Drawings

1

CATALYTIC OXIDATIVE DEHYDROGENATION OF ALKYLAROMATICS AND PARAFFINS

The invention relates to a process for the preparation of olefinically unsaturated compounds by catalytic oxidation/ oxidative dehydrogenation by transferring oxygen from a previously oxidized oxygen carrier acting as catalyst in the absence of molecular oxygen. The invention preferably relates to the catalytic oxidative dehydrogenation of alkylaromatics and paraffins to form the corresponding alkenyl aromatic compounds and olefins, in particular the dehydrogenation of ethyl benzene to styrene with the formation of water.

Styrene and divinyl benzene are important monomers for industrial plastics and are used in large quantities.

Styrene is prepared over modified iron oxide catalysts mainly by non-oxidative dehydrogenation of ethyl benzene, one mole of hydrogen being formed per mole of styrene. Unfortunately this reaction is an equilibrium reaction which takes place at temperatures typically of from 600° to 700° C. and proceeds at a conversion of ca 60% and a styrene selectivity of approximately 90%, the reverse reaction commencing with increasing conversion and increasing concentration of the target product, which factor thus restricts the final degree of conversion.

By contrast, the use of oxidative dehydrogenation, in which the hydrocarbon to be converted is caused to react with molecular oxygen, ie generally air, produces almost quantitative conversion, since in this case water is formed. In addition this reaction takes place at a lower temperature than the non-oxidative dehydrogenation. A drawback of the oxidative dehydrogenation using molecular oxygen is that total oxidation takes place as a side reaction, with the result that carbon dioxide and further amounts of water occur in the product stream. This phenomenon is frequently referred to as "gasification".

It has therefore been proposed to use an oxygen carrier consisting of a reducible metal oxide which acts as catalyst, ie has an influence on the reaction, instead of molecular oxygen. The oxygen carrier undergoes continuous exhaustion and has to be regenerated in a second step to restore the initial activity. This method is frequently used in classical process engineering and is known as the regenerative technique. In the reactivation phase any coke deposits, for example, can also be calcined. The regeneration process is highly exothermal, so that the liberated waste heat can be utilized for the production of steam, for example. By decoupling the reduction and oxidation steps the selectivity can be significantly increased.

From an engineering point of view there are two ways of effecting decoupling, ie spatial and temporal separation of the two partial steps.

When effecting spatial separation of the two partial steps a moving bed is used, the catalyst particles being conveyed from the dehydrogenation zone to a separate regenerating reactor, following separation of the reaction products, in which regenerating reactor reoxidation takes place. The regenerated catalyst is recycled to the dehydrogenation zone. Such a process can be set up for continuous, ie cyclical operation. The catalyst is exposed to high mechanical stresses and must therefore possess adequate hardness.

Temporal separation can be realized when using a fixed bed oxygen carrier by switching periodically between the useful reaction and the regeneration, optionally following a purging phase using inert gases.

The principle of regeneration using a reducible and reactivatable catalyst was first described for the oxidation or ammonoxidation of propene to produce acrolein and acrylic acid or acrylonitrile respectively (GB 885,422; GB 999,629; K. Aykan, *J. Catal.* 12 (1968) 281–190), arsenate and molybdate catalysts being used. The use of the regenerative method in the oxidative dehydrogenation of aliphatic alkanes to produce mono- and di-olefins using ferrite catalysts (eg. U.S. Pat. No. 3,440,299 DE 2,118,344, DE 1,793, 499) is likewise known, as is also the use thereof for the oxidative coupling of methane to form higher hydrocarbons; catalysts of various structures are used in this process (U.S. Pat. No. 4,795,849, DE 3,586,769 using Mn/Mg/Si oxides; U.S. Pat. No. 4,568,789 using Ru oxide; EP 254,423 using Mn/B oxides on MgO; GB 2,156,842 using $Mn_3O_4$ spinels). Also the dehydrodimerisation of toluene to produce stilbene in the absence of free oxygen by means of reducible catalysts such as Bi/In/Ag oxides (EP 30,837) is known.

Finally the principle is still employed for the dehydrogenation, dehydrocyclisation, and dehydroaromatisation of paraffins for the improvement of gasoline (U.S. Pat. No. 4,396,537 using Co/P-oxide catalysts).

EP 397,637 and 403,462 disclose that it is possible to use this type of process for the oxidative dehydrogenation of paraffins and alkylaromatics. According to said references reducible metal oxides are used, selected from the group consisting of V, Cr, Mn, Fe, Co, Pb, Bi, Mo, U, and Sn, applied to supports composed of clays, zeolites and oxides of Ti, Zr, Zn, Th, Mg, Ca, Ba, Si, Al.

Although a high yield is reportedly obtained with these catalysts, very intense gasification (total combustion) occurs in the initial phase of the dehydrogenation, when the hydrocarbon comes into contact with the freshly regenerated catalyst. Apart from the loss of raw materials there is the further consideration that considerably more oxygen is consumed than for the mere dehydrogenation, so that the oxygen carrier becomes prematurely exhausted and the cycle period decreases unnecessarily.

EP 482,276 has therefore proposed the partial prereduction of the freshly regenerated catalyst, for example using $H_2$ or CO, before the catalyst is brought into contact with the starting hydrocarbon in the dehydrogenation zone. This measure does indeed improve the initial selectivity, but the process requires an additional step and the use of an expensive reducing agent which is foreign to the reaction. The problem of initial gasification apparently also exists in other oxidation reactions carried out industrially using redox systems, for the partial prereduction of the catalyst as remedial action has also been proposed elsewhere (cf JA 127,819).

Thus, when this reaction concept is to be utilized industrially, it is particularly important to suppress the initial total oxidation as far as possible. According to a proposal not prepublished this is made possible with certain catalysts by means of special temperature control and the use of a special procedure during the operating and regenerating phases.

However regenerative techniques of the aforementioned nature have yet another drawback: if they are to provide high space-time yields, either the individual cycle periods are short, since the catalyst, as may be appreciated, can only absorb relatively small quantities of oxygen, or the amount of catalyst must be increased, ie the reactors used must be particularly large. Thus it is necessary to choose between high-wearing frequent switching on the one hand and high investment on the other hand.

It is the object of the present invention to provide a process which reduces the gasification in the initial phase of the dehydrogenation, increases the selectivity toward the desired product, and can do without elaborate additional process engineering steps such as partial prereduction using an expensive reducing agent such as $H_2$, CO, etc. And which operates to produce a very favorable space-time yield.

We have now found that a process of the kind defined above achieves the aforementioned objects to particular advantage by effecting adjustment, ie control, during the operating phase of the catalyst (oxidation/dehydrogenation step), of the residence time, space velocity, and/or temperature of the reactants in the reactor, continuously or in discrete steps, in a manner appropriate to the momentary state of activity of the redox catalyst, such that the residence time of the reactant in the freshly regenerated catalyst (ie at the commencement of the reaction) is adjusted—continuously or stepwise—to a shorter time or the space velocity is adjusted to a higher value, and/or the temperature is adjusted to a lower value than the corresponding parameter(s) in the partially reduced catalyst. To use a graphic illustration, each of said parameters thus passes over a "wedge" or inclined plane, either upwardly or downwardly as may be.

It should be noted that when using an undiluted feed of the starting mixture a change in residence time is a variable which is reciprocal to change in space velocity; a change of residence time can thus be influenced by a corresponding modification of the space velocity. Dilution with an inert gas makes it possible to influence residence time and space velocity independently of each other.

In addition the regeneration of a conventional redox catalyst (oxygen carrier) to form a fresh catalyst produces a distinctly reduced tendency to initial gasification and thus an improvement of the initial selectivity if the spent (reduced) catalyst is cooled, prior to reoxidation, ie prior to the introduction of the regenerative stream either still in the presence of the reaction mixture having a reducing action, ie in the presence of the educt itself, or, preferably, under a blanket of inert gas (which can be the same as the purging gas), to a temperature $T_{reg}$, which is below the temperature of the reaction $T_{react}$ and regeneration is commenced at said (lower) temperature $T_{reg}$ by the introduction of the oxidizing agents, ie, in particular oxygen, air, impoverished air, or $N_2O$, regeneration being controlled in such a manner that the highest temperature occurring during regeneration, the so-called hot-spot temperature, does not exceed the temperature of reaction $T_{react, o}$ at which reoxidation is commenced.

Following the removal of the oxidizing environment, ie in the absence of the oxidizing agents, preferably under a blanket of inert gas, which may if desired be identical to the purging gas, the regenerated catalyst is heated to the (initial) reaction temperature $T_{react, o}$ and only then is the reaction started by the introduction of the hydrocarbon (educt).

The method of the invention is described below in greater detail:

The operating phase of the catalyst is advantageously controlled in such a manner that at the commencement of the reaction, ie when the starting material to be oxidized (the educt) comes into contact with the freshly regenerated catalyst, the residence time set is so short that when (for example) quantitative conversion is just achieved initial yield is at a maximum and initial gasification is at a minimum. As the reaction proceeds and the degree of oxidation of the catalyst declines, the residence time is made increasingly longer and is adapted to the momentary state of the catalyst in such a manner that quantitative conversion is just reached at all times. To this end the residence time has to be increased during the reaction continuously or progressively. The optimal residence time wedge is generally not a linear function of time, although this alone would yield results which are better than in the prior art. According to the invention, however, the graph of the optimal residence time plotted against time is curved (see Table 1 below). It will be appreciated that the invention is not restricted to operating conditions which produce only just quantitative conversion during each portion of the operating phase, but rather it is possible to adjust the conditions to give incomplete conversion if this is meaningful from the point of view of other structural factors of a given industrial plant (with recycling of a partial stream).

Similar considerations to those discussed above applying to residence time and reciprocal space velocity (SV=space velocity) naturally also apply to the temperature: the temperature of reaction is, if necessary, increased during the operating phase and/or the space velocity is decreased. At the beginning of the reaction, ie immediately following regeneration, the temperature is at its lowest and the space velocity at its highest.

Industrially accepted oxidation/dehydrogenation processes are carried out at temperatures of reaction ranging from 100° to 900° C. and preferably from 250° to 750° C. and at pressures ranging from 100 mbar to 10 bar and preferably from 500 mbar to 2 bar, the LHSV (liquid hourly space velocity) being from 0.01 to 20 $h^{-1}$ and preferably from 0.1 to 5 $h^{-1}$ based on the liquid state of aggregation. In addition to the hydrocarbon to be oxidized/dehydrogenated there can be present diluents such as $CO_2$, $N_2$, noble gases, or steam.

The regeneration of the spent catalyst is carried out at temperatures in the range of from 100° to 800° C. and preferably from 250° to 600° C. using a free oxidizing agent, preferably $N_2O$ or an oxygen-containing gas, including pure oxygen. Here again diluents can be present in the regeneration stream. Suitable regenerating gases are, eg, air, impoverished air, oxygen, or $N_2O$. The regeneration can be carried out under subatmospheric, atmospheric, or superatmospheric pressure. Pressures ranging from 500 mbar to 10 bar are preferred.

The wedge (range of variations) of the residence time is generally from 0.01 s to 20 s and preferably in a range of from 0.05 s to 10 s and more preferably in a range of from 0.1 s to 5 s.

The range of variations of the LHSV (LHSV wedge) generally extends from 0.01 $h^{-1}$ to 20 $h^{-1}$ and preferably from 0.05 $h^{-1}$ to 10 $h^{-1}$ and more preferably from 0.1 $h^{-1}$ to 5 $h^{-1}$. The wedge (range of variations) of the temperature generally ranges from room temperature to 900° C. and preferably from 100° C. to 700° C. and more preferably from 200° C. to 600° C.

The method of running the reaction using "wedged" residence-time, temperature, and space-velocity profiles is demonstrated below by way of example with reference to the unsteady oxidative dehydrogenation of ethyl benzene to styrene, but, as stated above, it is also applicable to other oxidation reactions, it being necessary, in each case, to take into consideration the characteristics of the system being used, as regards type of catalyst and reaction conditions.

Suitable catalysts for use in the above process are theoretically all catalysts containing reducible metal oxides such as oxides of Bi, V, Ce, Fe, Cr, In, Ag, Cu, Co, Mn, Pb, Sn, Mo, W, As, Sb, preferably Bi oxide, Ce oxide, and V oxide, and more preferably $Bi_2O_3$ or $CeO_2$ and which can be used as supported or unsupported catalysts. The supports used are preferably oxides of transition metals such as titanium oxide or chromium oxide, preferably $TiO_2$ and $Cr_2O_3$.

A suitable catalyst contains or consists of, for example, from 5 to 60 wt %, preferably from 10 to 45 wt % of vanadium, from 10 to 95 wt %, preferably from 30 to 80 wt % of chromium or titanium and from 1 to 40 wt %, preferably from 3 to 20 wt % of alkali metal and/or alkaline earth metal and/or a rare earth (always determined in terms of the most stable oxide) and contains, when chromium oxide is used as support, from 0 to 70 wt %, preferably from 10 to 50 wt %, of a catalytically ineffective oxide ie an inorganic binding agent, preferably an aluminum oxide. The above proportions also apply to the aforementioned other elements which can be used instead of vanadium.

Another favorable catalyst contains or consists of from 5 to 60 wt %, preferably from 10 to 45 wt % of cerium(IV) oxide on a support consisting of from 10 to 95 wt %, preferably from 20 to 80 wt %, of chromium(III) oxide with from 1 to 40 wt %, preferably from 3 to 20 wt %, of alkali metal and/or alkaline earth metal (determined as oxide) and contains from 0 to 70 wt %, preferably from 10 to 60 wt %, of aluminum oxide.

A particularly preferred catalyst contains or consists of from 5 to 60 wt %, preferably from 10 to 45 wt %, of bismuth(III) oxide, from 5 to 25 wt %, preferably from 10 to 20 wt %, of lanthanum(III) oxide, from 10 to 95 wt %, preferably from 30 to 80 wt %, of titanium(IV) oxide, which is regarded as support, and from 1 to 40 wt %, preferably from 3 to 20 wt % of alkali metal and/or alkaline earth metal.

The above proportions relate to the finished catalyst in its most stable oxidation stage or in the oxidation stage stated. Thus the above is not intended to imply statements on the actual bonding ratios, to which the invention is not restricted; for example, during calcination other phases can form which correspond to higher oxidation stages but are not actually oxides, such as chromates or bichromates of potassium or bismuth.

The catalyst can be prepared in the usual manner such as by dry mixing, slurrying, impregnation, precipitation, spray drying, etc. The ingredients can be used, eg, in the form of their oxides, hydroxides, carbonates, acetates, nitrates or generally water-soluble salts with organic or inorganic anions, which convert on heating (calcination) to the corresponding oxides. Transition metal complexes can also be used, for example. Calcination is carried out at temperatures in the range of from 200° to 1000° C., preferably from 200° to 800° C. and in particular from 400° to 700° C.

The regeneration or reactivation of the catalyst is carried out at temperatures in the range of from 100° to 600° C., preferably from 250° to 500° C. using a molecular oxidizing agent. Examples of suitable agents are air, impoverished air, oxygen, and $N_2O$. A diluent can also be used. Regeneration can be carried out under reduced pressure or under atmospheric or superatmospheric pressure. Pressures are preferred in the range of from 500 mbar to 10 bar.

The process of the invention is demonstated below by way of example with reference to the unsteady oxidative dehydrogenation of ethyl benzene to form styrene, but is perfectly applicable to other oxidation reactions.

EXAMPLE 1

The action of the residence time wedge on the unsteady oxidative dehydrogenation of ethyl benzene was demonstated in a saline-cooled fixed bed reactor having a catalyst capacity of 20 ml. The reactor temperature was 500° C. Linear optimization in the residence time/temperature (RT/T) parameter configuration gave, for a maximum integral styrene yield as response value, the optimal reaction parameters T=500° C. and RT=1.6. The space velocity (LHSV) was 1 0.5 $h^{-1}$ (10 ml of ethyl benzene per hour). The residence time was varied by causing dilution with nitrogen in a controlled manner (of course care was taken to ensure complete absence of free oxygen). The catalyst consisted of 15% of $K_2O$, 15% of $La_2O_3$, 25% of $Bi_2O_3$ and 45% of $TiO_2$. An off-line gas chromatographic analysis of the liquid effluent was carried out (no gas present). A sample was taken once a minute after the appearance of the first liquid effluent. Table 1 shows the results.

TABLE 1

| Sample No. | Reaction Time [min] | Variable RT 0.7→1.8 [s] | Styrene Yield [wt %] | Fixed RT RT = 1.6 [s] | Styrene Yield [wt %] |
|---|---|---|---|---|---|
| 1 (1st liquid effluent) | 4 | 0.7 | 95.6 | 1.6 | 93.9 |
| 2 | 5 | 0.7 | 96.1 | 1.6 | 94.5 |
| 3 | 6 | 0.9 | 96.3 | 1.6 | 95.3 |
| 4 | 7 | 1.2 | 95.4 | 1.6 | 95.2 |
| 5 | 8 | 1.5 | 93.8 | 1.6 | 91.0 |
| 6 | 9 | 1.8 | 88.3 | 1.6 | 81.5 |

Examination of the table gives the following conclusions: compared with the results obtained when using a fixed residence time (regarded as optimal in the prior art) there was, due to the use of a residence time wedge, an improvement in the initial styrene selectivity, an increase in the maximum styrene yield, and prolongation of the cycle periods (slower deactivation).

EXAMPLE 2

The catalyst described in Example 1 was used.

The action of the temperature wedge on the catalytic oxidative dehydrogenation of ethyl benzene to produce styrene was carried out in a pulsating reactor at reaction temperatures in a range of 465°–550° C. In this process a fixed micro bed was acted upon (initial weight of catalyst: 0.3–0.6 g) pulsation being caused by pure ethyl benzene in the total absence of free oxygen, and the resulting reaction products were examined by quantitative gas-chromatographic analysis for each pulse. Helium flowed as carrier gas through the reactor between two successive ethyl benzene pulses (ca 1.5 min). An individual pulse contained 380 µg of ethyl benzene. The rate of flow of the carrier gas was 21.5 ml/min. In this way deactivation of the catalyst could be monitored at a high time resolution and without the occurrence of dead times right from the start.

At the commencement of the reaction the catalyst was highly active so that high conversions of ethyl benzene were observed. Due to an increased formation of by-products (eg, gasification to carbon oxides) the high initial activity often led to losses of selectivity toward styrene. As the reaction proceeded, the formation of by-products declined and the selectivity toward styrene then improved constantly up to a final value typical of the catalyst under consideration. As the time of the experiment increased the catalyst was progressively deactivated at the rate at which its grid oxygen was consumed, so that the ethyl benzene conversion sank. Regeneration was carried out after 90 pulses. The results show that the yield of styrene, in terms of the product of selectivity and conversion, generally passes through a flat peak.

On completion of the dehydrogenation reaction the regeneration of the spent, ie reduced, catalyst was carried out as proposed for the process of the invention. A new dehydrogenation cycle followed using the reactivated catalyst. Several cycles were run.

For all catalysts under consideration the catalytic activity could be restored to its full extent by reoxidation of the deactivated, reduced catalysts. No loss of activity increasing with on-stream time was found. Table 2 shows the results.

TABLE 2

| | | T Wedge | Fixed Reactor Temperature | | |
|---|---|---|---|---|---|
| Pulse No. | T Wedge [°C.] | Styrene T = 465→510° C. [%] | Styrene T = 480° C. [%] | Styrene T = 490° C. [%] | Styrene T = 500° C. [%] |
| 1 | 465 | 85.5 | 74.2 | 73.0 | 69.2 |
| 4 | 470 | 92.5 | 90.7 | 87.7 | 84.3 |
| 7 | 475 | 92.5 | 91.4 | 89.0 | 86.1 |
| 10 | 480 | 92.5 | 92.2 | 91.1 | 87.9 |
| 20 | 485 | 93.3 | 93.5 | 92.5 | 91.4 |
| 30 | 490 | 93.3 | 93.7 | 93.4 | 92.7 |
| 40 | 495 | 92.2 | 91.6 | 92.0 | 89.2 |
| 50 | 500 | 89.0 | 83.7 | 83.8 | 77.8 |
| 60 | 505 | 80.7 | 72.3 | 70.9 | 66.2 |
| 70 | 505 | 68.3 | 60.5 | 60.2 | 60.1 |
| 80 | 510 | 65.7 | 52.9 | | |

Table 2 shows the following: the T wedge impoved the initial selectivity, lowered the initial gasification, achieved throughout higher overall selectivity and a longer cycle period ie retarded deactivation and improved the catalyst efficiency.

EXAMPLE 3

Example 2 was repeated except that the regeneration was carried out at a lower temperature than the dehydrogenation: on completion of the reaction (90th pulse) the reactor was cooled under a blanket of helium to 380° C., the regeneration was then started (45 min with air, gas flow rate ca 25 ml/min), followed by a switch from air to helium (gas flow rate ca 21 ml/min of He) and reheating under a blanket of helium to the initial reaction temperature of Example 2, followed by evaluation as described above. Table 3 shows the results.

TABLE 3

| Pulse No. | T Wedge 1 [°C.] | Styrene 1 [%] | T Wedge 2 [°C.] | Styrene 2 [%] |
|---|---|---|---|---|
| 1 | 470 | 91.9 | 470 | 90.4 |
| 4 | 473 | 92.7 | 475 | 92.3 |
| 7 | 476 | 92.5 | 480 | 91.9 |
| 10 | 480 | 93.0 | 483 | 92.0 |
| 20 | 485 | 93.6 | 488 | 92.9 |
| 30 | 490 | 94.0 | 495 | 92.9 |
| 40 | 500 | 93.0 | 505 | 92.7 |
| 50 | 510 | 90.4 | 520 | 90.8 |
| 60 | 520 | 85.2 | 540 | 87.7 |
| 70 | 530 | 80.8 | 550 | 82.0 |
| 80 | 530 | 74.0 | 550 | 76.9 |
| 90 | 550 | 75.3 | | |

Table 3 shows the results achieved when the T wedge of the invention is combined with the aforementioned regeneration process.

It is seen that the problem of high initial gasification and poor initial selectivity was completely eliminated. The very first pulse gave a styrene yield of better than 90%.

EXAMPLE 4

The action of the LHSV-wedge on the unsteady oxidative dehydrogenation of ethyl benzene was demonstated in a saline-cooled fixed bed reactor having a catalyst capacity of 20 ml. The reactor temperature was 500° C. and the residence time 1.2 s. Linear optimization using the maximum integral styrene yield as response value had given, in the residence time/temperature parameter configuration, T=500° C. and residence time=1.2 s as the optimal reaction parameters. Adjustment of the residence time was effected by a stream of $N_2$ as diluent gas (complete absence of free oxygen). When space-velocity wedges were used the LHSV was continuously lowered during dehydrogenation from 0.7 or 0.8 $h^{-1}$ respectively to 0.3 $h^{-1}$. For purposes of comparison tests were carried out at constant space velocities (LHSV) of 0.7, 0.6, 0.5, 0.4 and 0.3 $h^{-1}$ (an LHSV of 0.5 $h^{-1}$ corresponds to, eg, 10 ml of ethyl benzene per hour; cf Table 4a). The adjustment of the LHSV was carried out by means of a regulated HPLC feed pump for ethyl benzene. The catalyst consisted of 12.5% of $K_2O$ 15% of $La_2O_3$ 25% of $Bi_2O_3$ 47.5% of $TiO_2$. An off-line gas-chromatographic analysis of the liquid effluent was carried out (no gas present). A sample was taken once a minute after the appearance of the first liquid effluent. Tables 4 and 4a show the results.

TABLE 4

| Sample No. | Reaction Time [min] | LHSV Wedge 1 [l/h] | Styrene SV Wedge 1 [wt %] | LHSV Wedge 2 [l/h] | Styrene SV Wedge 2 [wt %] |
|---|---|---|---|---|---|
| 1 | 4 | 0.7 | 94.2 | 0.8 | 94.4 |
| (1st liquid effluent) | | | | | |
| 2 | 5 | 0.5 | 94.7 | 0.6 | 94.6 |
| 3 | 6 | 0.4 | 95.0 | 0.4 | 94.5 |
| 4 | 7 | 0.3 | 96.7 | 0.3 | 94.3 |
| 5 | 8 | 0.3 | 93.5 | 0.3 | 92.2 |
| 6 | 9 | 0.3 | 91.2 | 0.3 | 90.8 |
| 7 | 10 | 0.3 | 86.0 | 0.3 | 86.3 |
| 8 | 11 | 0.3 | 78.1 | 0.3 | 79.8 |
| 9 | 12 | 0.3 | 66.8 | | |
| 10 | 13 | 0.3 | 56.7 | | |

TABLE 4a

| Sample No. | Reaction Time [min] | Styrene in Percent by Weight | | | | |
|---|---|---|---|---|---|---|
| | | LHSV = 0.7 [h⁻¹] | LHSV = 0.6 [h⁻¹] | LHSV = 0.5 [h⁻¹] | LHSV = 0.4 [h⁻¹] | LHSV = 0.3 [h⁻¹] |
| 1 (1st liquid effluent) | 4 | 94.4 | 93.4 | 92.6 | 94 | 91.7 |
| 2 | 5 | 94.1 | 94.3 | 94.1 | 94.5 | 92.9 |
| 3 | 6 | 90.2 | 91.8 | 94.8 | 95 | 94 |
| 4 | 7 | 80.1 | 85.3 | 93.5 | 93.9 | 94.8 |
| 5 | 8 | 65.5 | 74 | 89.4 | 91.1 | 95 |
| 6 | 9 | 53.4 | 61.5 | 82.4 | 84.5 | 94.1 |
| 7 | 10 | | 50.9 | 73.5 | 74.1 | 90.9 |
| 8 | 11 | | | 60.2 | 63.2 | 83.9 |
| 9 | 12 | | | | | 70.6 |
| 10 | 13 | | | | | 56.2 |

Table 4 demonstrates the following: when a high space velocity is set in the initial phase of the dehydrogenation, the initial selectivity can be improved. As the reaction proceeds the space velocity is constantly decreased such that at all times only just quantitative conversion is maintained. Unconverted amounts of educt can be minimized in this way and there is no need to use, eg. the elaborate separation of ethyl benzene and styrene which is the general practice in industrial processes (it should be remembered that the boiling points of ethyl benzene and styrene are very similar).

Compared with the mode of operation involving high (constant) space velocities the mode of operation of the invention leads to slower deactivation and a longer cycle period resulting in improvement of catalyst efficiency. Higher total yields are achieved per cycle.

Table 4a demonstrates the following: the initial selectivity is improved over the use of low space velocity. The catalyst efficiency is improved over the use of high space velocity. An overall higher yield is achieved.

Another advantage of the reaction procedure of the invention is the possibility of being able to lower the basicity of the redox catalyst: by reducing the alkali content of the catalyst a loss of initial selectivity occurs, which, however, can be compensated by the measures of the present invention, whilst a smaller alkali content causes, in advantageous manner, a prolongation of the cycle period, since the net weight of the catalyst can be adjusted to a higher value.

We claim:

1. A process for the preparation of olefinically unsaturated compounds by catalytic oxidation/oxidative dehydrogenation by transferring oxygen from a previously oxidized oxygen carrier acting as catalyst, in the absence of molecular oxygen, the catalyst being regenerated after exhaustion, wherein, during the operating phase of the catalyst (oxidation/dehydration partial step), the residence time, space velocity, and/or temperature of the reactants in the reactor is/are continuously, or in discrete steps, adapted to the momentary state of activity of the redox catalyst such that the residence time of the reactants in the freshly regenerated catalyst (ie at the commencement of the reaction) is adjusted to a shorter value or the space velocity is adjusted to a higher value, and/or the temperature is adjusted to a lower value than the corresponding parameter (s) in the partially reduced catalyst, said adjustments being effected continuously or in steps.

2. A process as defined in claim 1, wherein the catalytic oxidative dehydrogenation of alkylaromatics and paraffins is carried out to produce the corresponding alkenylaromatic compounds and olefins.

3. A process as defined in claim 1, wherein the dehydrogenation of ethyl benzene is carried out to produce styrene.

4. A process as defined in claim 1, wherein a catalyst is used which contains at least one supported or unsupported reducible metal oxide selected from the group consisting of the oxides of Bi, V, Ce, Fe, In, Ag, Cu, Co, Mn, Pb, Sn, Mo, W, As, and/or Sb.

5. A process as defined in claim 4, wherein the support used for the catalyst is an oxide of a transition metal such as titanium oxide or chromium oxide.

6. A process as defined in claim 4, wherein the redox catalyst used is of the class $Bi_2O_3/TiO_2$, which is preferably doped with an oxide of an alkali metal or alkaline earth metal and/or rare earth, in particular K and/or Cs and/or La.

7. A process as defined in claim 1, wherein temporal decoupling of the partial steps of the redox reaction is effected by using a fixed catalyst bed and causing periodic switching of the reactor influent between the educts and the regenerating gas.

8. A process as defined in claim 1, wherein between the oxidation/dehydrogenation step and the regenerating step there is inserted a purging phase in which a purging gas such as $CO_2$, $N_2$, $H_2O$, or a noble gas is caused to pass through the fixed bed reactor.

9. A process as defined in claim 1, wherein spatial decoupling of the partial steps of the redox reaction is carried out by causing the catalyst particles to be circulated, by means of a moving bed or a circulating fluidized bed, cyclically between an oxidation/dehydrogenation reactor and a separate regenerating reactor.

10. A process as defined in claim 1, wherein the oxidation/oxidative dehydrogenation is carried out at temperatures between 200° and 900° C. and in a pressure range of from 100 mbar to 10 bar using a space velocity (LHSV) of from 0.01 to 20 $h^{-1}$, and the regeneration is effected in a temperature range of from 100° to 700° C. and a pressure range of from 100 mbar to 50 bar.

11. A process as defined in claim 1, wherein the oxidation/oxidative dehydrogenation is carried out at temperatures between 300° and 600° C. and in a pressure range of from 500 mbar to 2 bar, using a space velocity (LHSV) of from 0.1 to 5 $h^{-1}$, and the regeneration is carried out in a temperature range of from 200° to 600° C. and a pressure range of from 500 mbar to 10 bar.

\* \* \* \* \*

UNITED STATES PATENT AND TRADEMARK OFFICE
CERTIFICATE OF CORRECTION

PATENT NO.: 5,780,700

DATED: July 14, 1998

INVENTOR(S): HAGEMEYER et al.

It is certified that error appears in the above-identified patent and that said Letters Patent is hereby corrected as shown below:

On the cover page, insert the following priority information:

--[30]   Foreign Application Priority Data

Oct. 12, 1994    [DE]   Germany ................ P 44 36 385.0--.

Signed and Sealed this

Fifth Day of December, 2000

Attest:

Q. TODD DICKINSON

*Attesting Officer*    *Director of Patents and Trademarks*